US012571783B2

(12) United States Patent
Nesch et al.

(10) Patent No.: US 12,571,783 B2
(45) Date of Patent: Mar. 10, 2026

(54) GAS DETECTOR WITH DETACHABLE ADAPTER

(71) Applicant: Dräger Safety AG & Co. KGaA, Lübeck (DE)

(72) Inventors: Volker Nesch, Lübeck (DE); Tim Blöcker, Lübeck (DE)

(73) Assignee: Drager Safety AG & Co. KGaA, Lübeck (DE)

( * ) Notice: Subject to any disclaimer, the term of this patent is extended or adjusted under 35 U.S.C. 154(b) by 238 days.

(21) Appl. No.: 18/366,888

(22) Filed: Aug. 8, 2023

(65) Prior Publication Data

US 2024/0053311 A1 Feb. 15, 2024

(30) Foreign Application Priority Data

Aug. 10, 2022 (DE) ..................... 10 2022 120 101.5

(51) Int. Cl.
*G01N 33/00* (2006.01)
(52) U.S. Cl.
CPC ................................ *G01N 33/0006* (2013.01)
(58) Field of Classification Search
CPC ................................................ G01N 33/0006
See application file for complete search history.

(56) References Cited

U.S. PATENT DOCUMENTS 6,232,357 B1 5/2001 Barbieri et al.
2003/0138329 A1* 7/2003 Koyano .................. G08B 21/14
417/63

FOREIGN PATENT DOCUMENTS

DE 60213012 T2 11/2006
WO WO-2013186131 A1 * 12/2013 ......... G01N 33/0006

OTHER PUBLICATIONS

Dichtungen & Stanzteile; WiCo Wichmann, Otto & Cie GmbH + Co. KG; Jan. 17, 2022, S. 1-2.
Viton® / FKM / FPM / Vollmaterial & Fluormoosgummi; HOKOSIL® Elastomertechnik GmbH; May 26, 2022, S. 1-2.

* cited by examiner

*Primary Examiner* — Laura Martin
*Assistant Examiner* — Anthony W Megna Fuentes
(74) *Attorney, Agent, or Firm* — McGlew and Tuttle, P.C.

(57) ABSTRACT

A gas detector (100) includes a housing (1), a sensor in the housing and an adapter (3, 3.1). An inlet in the housing provides a fluid connection between the sensor and the environment. The sensor is configured to measure a detection variable that correlates with the concentration of a target gas to be detected. The adapter (3, 3.1) can be detachably and fluid tightly mounted on the housing. A fluid guide unit can be connected to a connection element (12, 12.1) of the adapter (3, 3.1). When the adapter (3, 3.1) is attached, an elastic filling (6, 6.1) is located between an outer shell (9, 9.1) of the adapter (3, 3.1) and the sensor. The filling (6, 6.1) is made of a cured foam. The foam includes fluorinated rubber. A channel (10, 10.1) in the filling provides a fluid connection between the connection element (12, 12.1) and the sensor.

20 Claims, 5 Drawing Sheets

| 20:40 | ☑ ⟳→» | 🔋 |
|---|---|---|
| iBut | 0,18 | ppm |
| CO₂ | 0,105 | Vol% |
| ch₄ | 0 | %UEG |
| O₂ | 20,9 | Vol% |
| H₂S | 0 | ppm |
| CO | 0 | ppm |
| SO₂ | 0,0 | ppm |

100

GAS DETECTOR WITH DETACHABLE ADAPTER

CROSS REFERENCE TO RELATED APPLICATIONS

This application claims the benefit of priority under 35 U.S.C. § 119 of German Application 10 2022 120 101.5, filed Aug. 10, 2022, the entire contents of which are incorporated herein by reference.

TECHNICAL FIELD

The invention relates to a gas detector with at least one detachable adapter, wherein the gas detector is capable of detecting at least one specified target gas, in particular a combustible target gas.

BACKGROUND

Such a gas detector is used to detect a specified target gas in a spatial area and/or to measure the concentration of the target gas. In particular, the target gas is combustible or even explosive or in another way dangerous for humans.

SUMMARY

It is an object of the invention to provide a gas detector which can be adapted to different tasks more quickly than known gas detectors.

The object is attained by a gas detector having gas detector features according to the invention. Advantageous embodiments of the gas detector according to the invention are disclosed herein.

The gas detector according to the invention is configured to detect at least one specified target gas, optionally to detect several specified target gases simultaneously.

The gas detector includes a housing having at least one inlet. The housing encloses an interior space. The inlet or at least one inlet, preferably each inlet in the housing permanently or at least temporarily establishes or at least contributes to establishing a fluid connection between an environment of the gas detector and the interior space.

At least one sensor is arranged in the interior or at the interior. The sensor or each sensor is configured to measure a respective detection variable. This detection variable correlates with the presence and/or concentration of at least one target gas to be detected. Preferably, the detection variable is a current intensity or an electrical voltage or an electrical charge or an electrical resistance.

Furthermore, the gas detector comprises at least one adapter, preferably at least two adapters. The adapter or each adapter is mounted fluid-tightly on the housing or can be mounted fluid-tightly on the housing. The adapter or each adapter can be separated from the housing again. Preferably only one adapter can be mounted at one time point.

If the adapter or an adapter is attached to the housing, the attached adapter separates the inlet or each inlet fluid-tightly from the environment. If the adapter is attached, a gas sample from the environment cannot pass directly through the inlet into the interior and thus to a sensor, but only through the attached adapter. If no adapter is attached to the housing, the gas sample from the environment can pass directly through the inlet or at least one inlet into the interior and thus to the sensors.

The adapter or each adapter comprises a respective connection element. A fluid guide unit, in particular a hose, is connected to this connection element or can be connected, for example attached. If the adapter is attached to the housing, a gas sample can flow through the fluid guide unit and the connection element into the interior. Preferably, the fluid guide unit can be disconnected from the adapter again.

Furthermore, the adapter or each adapter comprises an outer shell and an elastic filling. When the adapter is attached, the elastic filling is located between the outer shell and the interior with the sensors. The elastic filling can be reversibly compressed.

The outer shell is made of a harder material than the elastic filling. The filling is made of a cured foam. This foam is a a fluororubber (fluorocarbon rubber, fluorinated rubber) or comprises at least one fluororubber.

A channel configuration with a least one channel is arranged in the filling, preferably several channels. Particularly preferably several channels are defined by the filling wherein the channels are free of intersections and/or parallel to each other. The channel or channels form a channel configuration. The channel or each channel establishes a fluid connection between the connection element and the sensor or each at least one sensor in the interior. It is possible that a first channel establishes a fluid connection between the connection element and a first sensor, and a second channel establishes a fluid connection between the connection element and a second sensor.

The gas detector according to the invention can be operated in a state in which the adapter or one adapter is attached to the housing. With the adapter being attached, a gas sample is allowed to flow through an external fluid guide unit connected to the connection element of the adapter and through the adapter into the interior and to the sensors. This configuration allows the interior of an at least partially enclosed space to be sampled for the target gas while positioning the gas detector outside of that space. Because the attached adapter fluid-tightly blocks the inlet or each inlet, no gas from the environment surrounding the gas detector can directly enter the interior. Gas from the environment could falsify the measurement if the enclosed space is to be investigated, for example if the particular space is to be measured, but not the surroundings.

Furthermore, the gas detector according to the invention can be operated in a state in which no adapter is attached, and a gas sample can flow directly from the environment into the interior. The gas detector then examines a gas sample from its environment.

The filling is made of an elastic material and faces the housing. This feature increases the reliability that the attached adapter actually separates the interior from the environment in a fluid-tight manner, even if the adapter is attached to the housing quickly and/or with gloves and/or in poor lighting conditions and is not guided by another component during fitting. In many cases the elastic material seals remaining gaps and slots between the adapter and the housing.

With the adapter being attached, the outer shell protects the filling to a certain extent against mechanical and chemical influences from the outside.

According to the invention, the filling of the adapter is made of a cured foam material. This feature makes it easier to bring the filling into a desired geometry than if another material were used, in particular a material that is solid and hard from the outset. In particular, it is easier to produce in the filling the channels for the fluid connections between the connection element and the sensors in the desired geometry.

According to the invention, the foam from which the filling is made is or comprises at least one fluorinated rubber.

A fluororubber is a rubber comprising vinyl (di)fluoride as a monomer. The fluororubber may in particular be provided as a copolymer of vinyl fluoride and hexafluoropropylene or as a terpolymer of vinyl fluoride, hexafluoropropylene and tetrafluoroethylene or comprise such a copolymer or ter- polymer in a proportion of at least 50% by weight, prefer- ably at least 80% by weight.

With the adapter is attached, a gas sample, which is to be analyzed for at least one target gas to be detected, flows from the connection element through the channel or channels in the filling to the interior and thus to the sensor or sensors. In many cases, the target gas is or includes long-chain hydro- carbons, particularly nonane. A nonane is an unbranched alkane having the molecular formula $C_9H_{20}$. In internal experiments, the inventors have found that a foam made of or comprising fluorinated rubber absorbs or binds long-chain hydrocarbons to a much lesser extent than other possible elastic materials. An essential reason is the molecular struc- ture of fluorinated rubber. Its molecular structure differs from the molecular structure of other potential materials and absorbs to a lesser extent several long-chained hydrocar- bons. A further reason for this is that the cured foam of or with fluorinated rubber forms a relatively smooth and closed surface which can quite easily be cleaned. One consequence of the molecular structure is that there is less risk than with other materials under consideration that, when a gas sample flows through the channels in the filling, the filling will absorb some of the target gas, which could lead to an incorrect measurement. In particular, absorption of target gas may result in a target gas not being detected.

It would be conceivable to take into account a possible absorption of target gas during a previous calibration and to calibrate the gas detector accordingly. However, this often has the following disadvantage: If the filling in a previous calibration were to absorb a relevant part of a target gas in a gas sample used for calibration, there would be a high risk that the concentration of a target gas in the gas sample inside the gas detector would be considerably lower than in the calibration station and therefore a false correlation between the target gas concentration and the detection variable would be generated. This can lead to incorrect measurement results.

For example, the correct relationship between the detec- tion variable U and the target gas concentration Con is $U=\alpha*Con$ with an empirically determined factor $\alpha>0$. If the filling absorbs half of the target gas, only the remaining half of the target gas reaches the sensors, and therefore the calibration results in the relationship $U=\alpha/2*Con$. When deployed, the gas detector will then use the relationship $Con=\alpha*U/2$, and therefore the gas detector would then measure twice the actual concentration if a target gas occurs that is not significantly absorbed by the fill. The gas detector will then give a relatively large number of false alarms.

Another source of error may occur when using a conven- tional elastic material for the filling if a target gas is used to calibrate the gas detector which is only slightly absorbed by the filling, for example methane, but the gas detector is used in an environment in which a target gas can occur which is absorbed to a considerable extent by the filling, in particular at least one long-chain hydrocarbon. There is a risk that the gas detector will not detect this target gas at relatively low concentrations. Calibration could become very costly and unreliable if every target gas under consideration had to be used for calibration. The invention reduces this risk.

The invention therefore avoids both the risk of not detect- ing a target gas and the risk of generating many false alarms.

In a preferred configuration, either a first adapter or a second adapter can be mounted on (attached to) the housing. The geometry of the connection surface between the adapter and the housing is the same for both adapters. Besides this, the adapters can have different configurations. In particular, the two adapters may comprise different connection ele- ments. This embodiment increases the flexibility of the gas detector. The same gas detector can selectively be connected to the first or to the second adapter, and it can also be connected successively first to one adapter and then to the other adapter.

In a further development, the connection element of the first adapter can be connected to an external fluid guide unit. An end of the fluid guide unit can thus be moved as described above into an at least partially enclosed space which is to be examined for a target gas to be detected. The connection element of the second adapter can be connected to a calibration station (gas detector calibration device). The gas detector with the attached second adapter is thereby connected to the calibration station. The calibration station supplies the connected gas detector with several gas samples, each sample a target gas to be detected containing with a known concentration. The respective value of the detection variable is recorded. In this way, an empirical relationship between the target gas concentration and the detection variable is derived, stored, and used later during an operation.

The two adapters can be adapted to the different dimen- sions and other requirements of the fluid guide unit and the calibration station, respectively.

In a preferred implementation, the filling of the adapter provides (defines) the respective wall for the channel or each channel through the adapter. Thus, the wall of the channel is not realized by a different material than the filling. In particular, the wall of the channel does not have the form of a tube made of a different material than the filling. This embodiment facilitates the manufacture of the filling com- pared to an embodiment in which at least one tube would have to be brought into the interior of the filling.

In a preferred embodiment, the outer shell is curved. It encloses a space. The filling completely fills this space, which is enclosed by the outer shell, except for the channel or channels. This configuration reduces the risk of turbu- lence occurring in the enclosed space, compared to a con- figuration in which there is a larger cavity in the enclosed space that is not occupied by the filling and does not function as a channel. This embodiment in turn increases the reli- ability of a measurement by the gas detector.

In the following, the invention is described by means of exemplary embodiments. The various features of novelty which characterize the invention are pointed out with par- ticularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
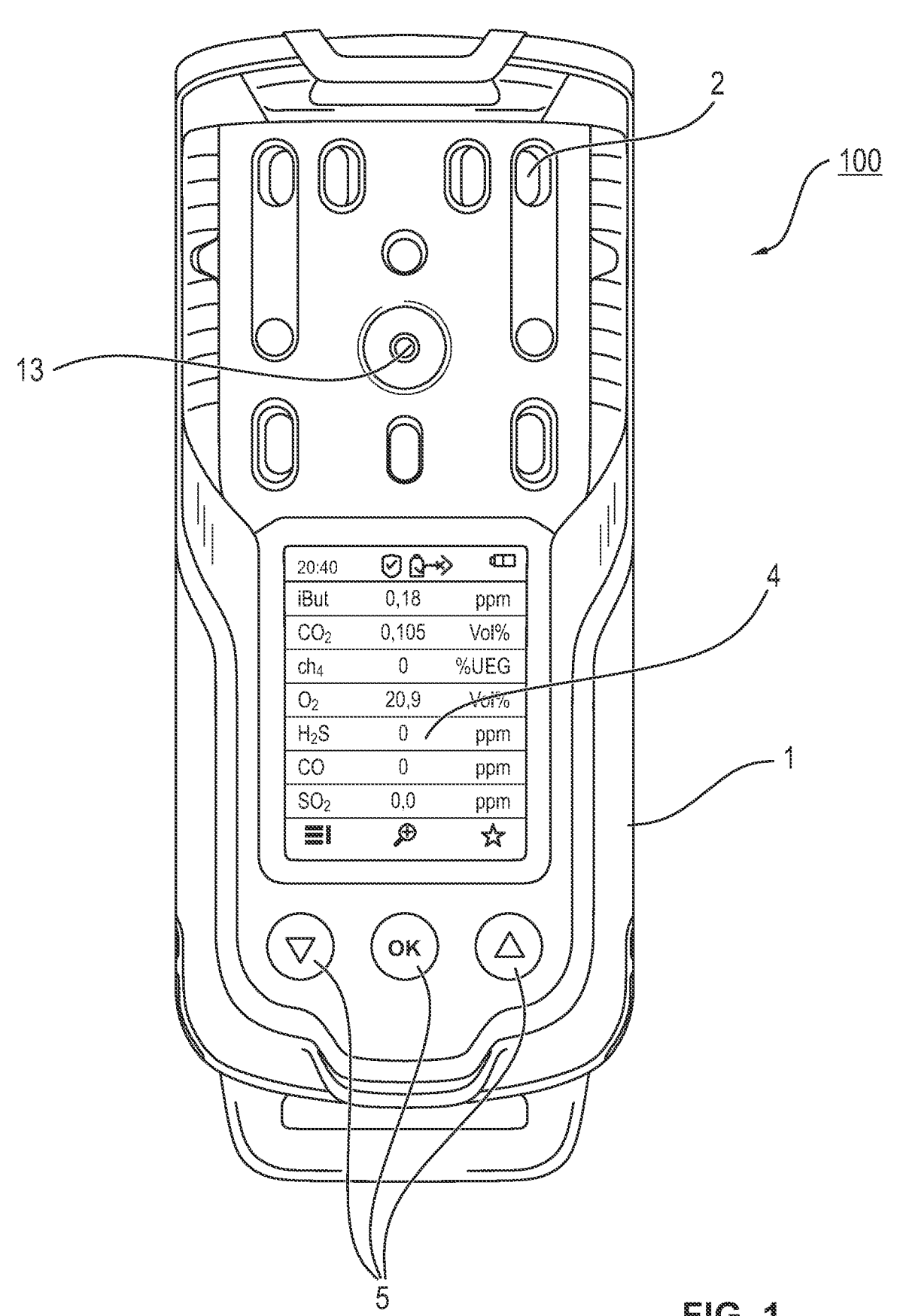
FIG. 1 is a top view the gas detector of the embodiment without adapter.

Referring to the drawings, in the embodiment example, the gas detector according to the invention is used to check a spatial area for the presence of at least one combustible target gas. In particular, the area may be an at least partially enclosed space or an outdoor area. The gas detector of the embodiment is configured to be carried by a human being.

Figure 2:
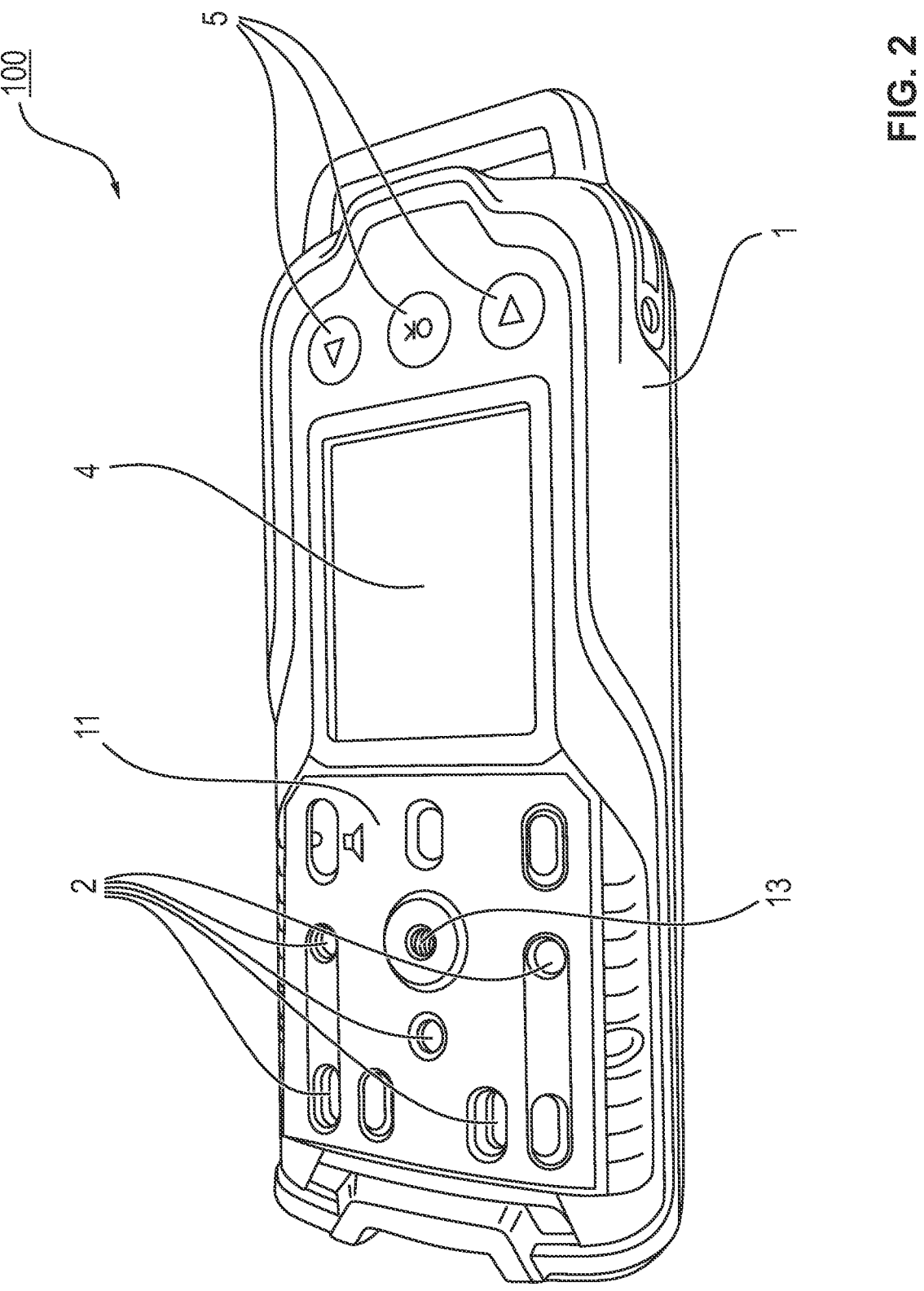
FIG. 2 is a perspective view of the gas detector of FIG. 1 with the adapter in place.

FIG. 1 and FIG. 2 show such a gas detector 100 in a top view and in a perspective view, respectively. A housing 1 encloses a measuring chamber and accommodates several sensors. A gas sample to be analyzed flows from the outside into the measuring chamber and reaches the sensors there. Preferably, the sensors are configured in such a way that the gas detector 100 is able to detect different combustible or otherwise harmful target gases.

The sensor or each of the sensors of the gas detector measure at least one detection variable, which detection variable correlates to the presence and/or concentration of a target gas to be detected. The detection variable is, for example, an electrical voltage or current or charge or resistance. A signal-processing evaluation unit derives an estimated value for the target gas concentration from the respective measured value of each detection variable.

A plurality of inlets 2 are recessed into the housing 1, which together provide a fluid connection between the environment and the sensors inside the housing 1. Furthermore, a display unit 4 and a plurality of operating elements 5 are recessed into the housing 1. On the display unit 4, the gas detector 100 is able to visually output several measurement results. As an example, the respective concentration of seven target gases is shown.

In one application, a fluid from the environment of the gas detector 100 diffuses through the inlets 2 to the sensors in the housing 1. This possibility is shown in FIG. 1.

An adapter 3 can be fitted fluid-tightly onto the inlets 2 in the housing 1. In FIG. 1, the adapter 3 is not attached. FIG. 2 illustrates the approximately rectangular area 11 above the inlets 2, with the attached adapter 3 covering the area 11. When the adapter 3 is attached to the housing 1, the adapter 3 covers and obstructs the area 11 and thus the inlets 2, so that when the adapter 3 is attached, there is no fluid connection between the sensors and the environment through the inlets 2. In FIG. 2, the inlets 2 are shown behind the area 11. Furthermore, a thread 13 for a screw of the adapter 3 can be seen in FIG. 1 and in FIG. 2.

The adapter 3 includes:

a hard outer shell 9 with a connection element in the form of a nozzle 12, an elastic filling 6 and one screw 14.

Figure 3:
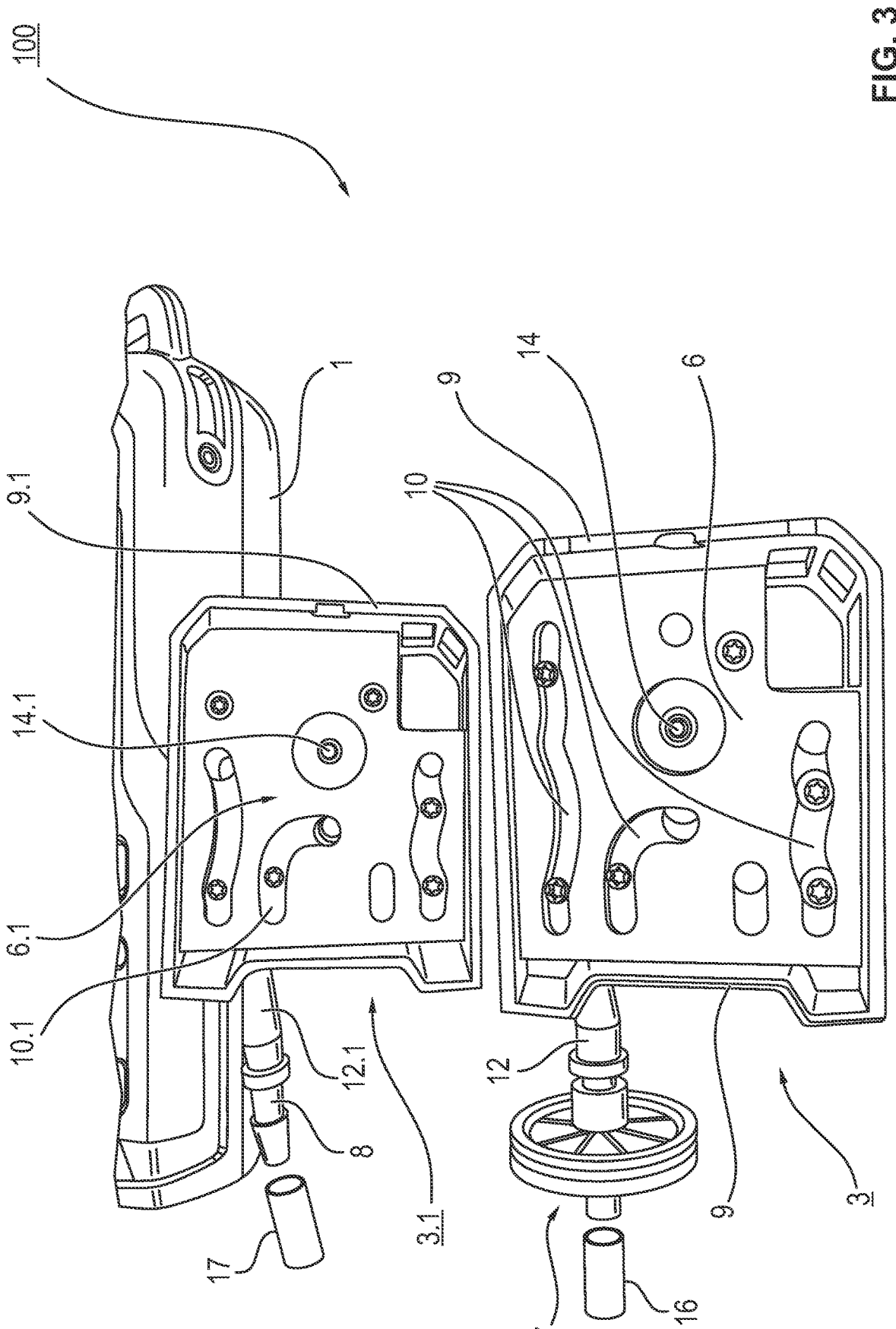
FIG. 3 is a perspective view showing the adapter (bottom) and the calibration adapter (top) in front of the gas detector of FIG. 1.

FIG. 3 shows the adapter 3 (bottom) and part of the housing 1 (top), with the elastic filling 6 facing the viewer.

With the adapter 3 in place, the screw 14 can be screwed into the thread 13. The filling 6 is then located between the outer shell 9 and the sensors. A plurality of fluid channels 10 are recessed in the filling 6. These fluid channels 10 establish fluid connections between the nozzle 12 and the sensors.

The outer shell 9 comprises a flat area and a curved area and encloses a space. The elastic filling 6 completely fills this space, except for the fluid channels 10. The filling 6 also provides the walls of the fluid channels 10.

A connection element 7 can be fitted onto the connecting piece (nozzle) 12 in a fluid-tight manner. This connection element 7 can be connected in a fluid-tight manner to a fluid guide unit, in particular to a hose 16. A fluid delivery unit, for example a pump, can be connected to the hose 16. It is also possible to connect the fluid delivery unit directly to the connection element 7. In another embodiment, the fluid delivery unit is arranged inside the housing 1.

Thanks to the hose 16 and the fluid delivery unit, the gas detector 100 is able to suck in a gas sample to be examined. The hose 16, the connection element 7, the nozzle 12 and the fluid channels 10 convey the aspirated gas sample to the sensors. It is possible that the gas sample originates from an enclosed space and the gas detector 100 is arranged outside this space. The adapter 3, which is attached in a fluid-tight manner, prevents gas from the environment of the gas detector 100 from reaching the sensors or prevents a gas sample from the interior of the housing 1 from reaching the environment.

Prior to a deployment, the gas detector 100 is calibrated. A calibration station, which is not shown, feeds at least one gas sample, preferably several different gas samples, to the gas detector 100, wherein the gas sample or each gas sample respectively contains a target gas to be detected with a known concentration. In one embodiment, the calibration station comprises at least one pressurized gas cylinder, wherein each pressurized gas cylinder contains a respective target gas with a known concentration. It is measured which value a detection variable of the gas detector 100 assumes for this gas sample. An empirical relationship between the target gas concentration and the detection variable is automatically derived from the measured values and the known concentrations. For example, a regression analysis is performed, or a neural network is trained.

Preferably, at least one gas sample contains methane and at least one gas sample contains propane. Preferably, at least one gas sample contains a long-chain hydrocarbon, for example nonane (molecular formula $C_9H_{20}$). Such long-chain hydrocarbons are often more difficult to detect than methane or propane. Therefore, it is advantageous if at least one gas sample also comprises a long-chain hydrocarbon so that the gas detector 100 is calibrated to detect long-chain hydrocarbons.

During calibration, another adapter 3.1 is placed on the housing 1 instead of the adapter 3. To distinguish it from the adapter 3 used during a use of the gas detector 100, this further adapter 3.1 is called "calibration adapter". The outer geometry of the calibration adapter 3.1 matches the outer geometry of the adapter 3, so that either the adapter 3 or the calibration adapter 3.1 can be inserted onto the housing 1.

The calibration adapter 3.1 includes:

a hard outer shell 9.1 with a connection element in the form of a nozzle 12.1, an elastic filling 6.1 and one screw 14.1.

FIG. 3 shows the calibration adapter 3.1 in the center, with the filling 6.1 facing the viewer.

The screw 14.1 can be screwed into the thread 13.

A plurality of fluid channels 10.1 are recessed in the filling 6.1. The filling 6.1 in turn occupies the entire space enclosed by the adapter 3.1, except for the fluid channels 10.1. The filling 6.1 provides the walls for the fluid channels 10.1.

A calibration connection element 8 can be mounted fluid-tightly on the connection piece 12.1. This calibration connection element 8 and an optional fluid guide unit, in particular a hose 17, make it possible to connect the calibration adapter 3.1 to the calibration station in a fluid-tight manner. A gas sample flows from the calibration station through the optional fluid guide unit, the calibration connection element 8 and the fluid channels 10.1 to the sensors.

The filling 6 of the adapter 3 and the filling 6.1 of the calibration adapter 3.1 are made of a foam material. This foam is placed in a flowable form in a hollow body, for example pressed, cures or is cured there, and is then removed again from the hollow body. The filling 6, 6.1 produced after curing is positively connected to the outer shell 9, 9.1, for example by bonding, or is screwed or held by a protrusion not shown. Of course, these forms of implementation can be combined with one another. Optionally, at least one plate is made of the foam, and several copies of the filling 6, 6.1 are cut out of this plate. By cutting out, each filling 6, 6.1 is given the desired peripheral contour.

In another embodiment, the foam is applied to the outer shell 9, 9.1 with a plurality of hollow bodies held near the inside of the outer shell 9, 9.1. The foam cures in the outer shell 9, 9.1. The hollow bodies cause the fluid channels 10, 10.1 to be formed. In addition, the foam bonds to the outer shell 9, 9.1 during curing.

Both manufacturing processes just mentioned make it easier to produce a filling 6, 6.1 with a desired geometry than with any other possible manufacturing process.

The foam from which the filling 6, 6.1 is made consists of at least one fluorinated rubber or comprises a fluorinated rubber. In this material, the sprayed skin of the foam forms a relatively smooth and closed surface.

An advantage resulting from the use of fluorinated rubber is the following: The filling 6, 6.1 absorbs long-chain hydrocarbons, for example nonane, to a significantly lesser extent than other possible materials, for example elastomers. Rather, the long-chain hydrocarbons flow through the fluid channels 10, 10.1 in the filling 6, 6.1 to the sensors. Because the filling 6, 6.1 according to the invention absorbs less hydrocarbon than other possible fillings, there is less risk that a measurement will be distorted or that the gas detector 100 will produce different results in use than during calibration. Also, less time is required for calibration, and in many cases, less gas is required for calibration. In use, the gas detector 100 detects a target gas more quickly.

Figure 4:
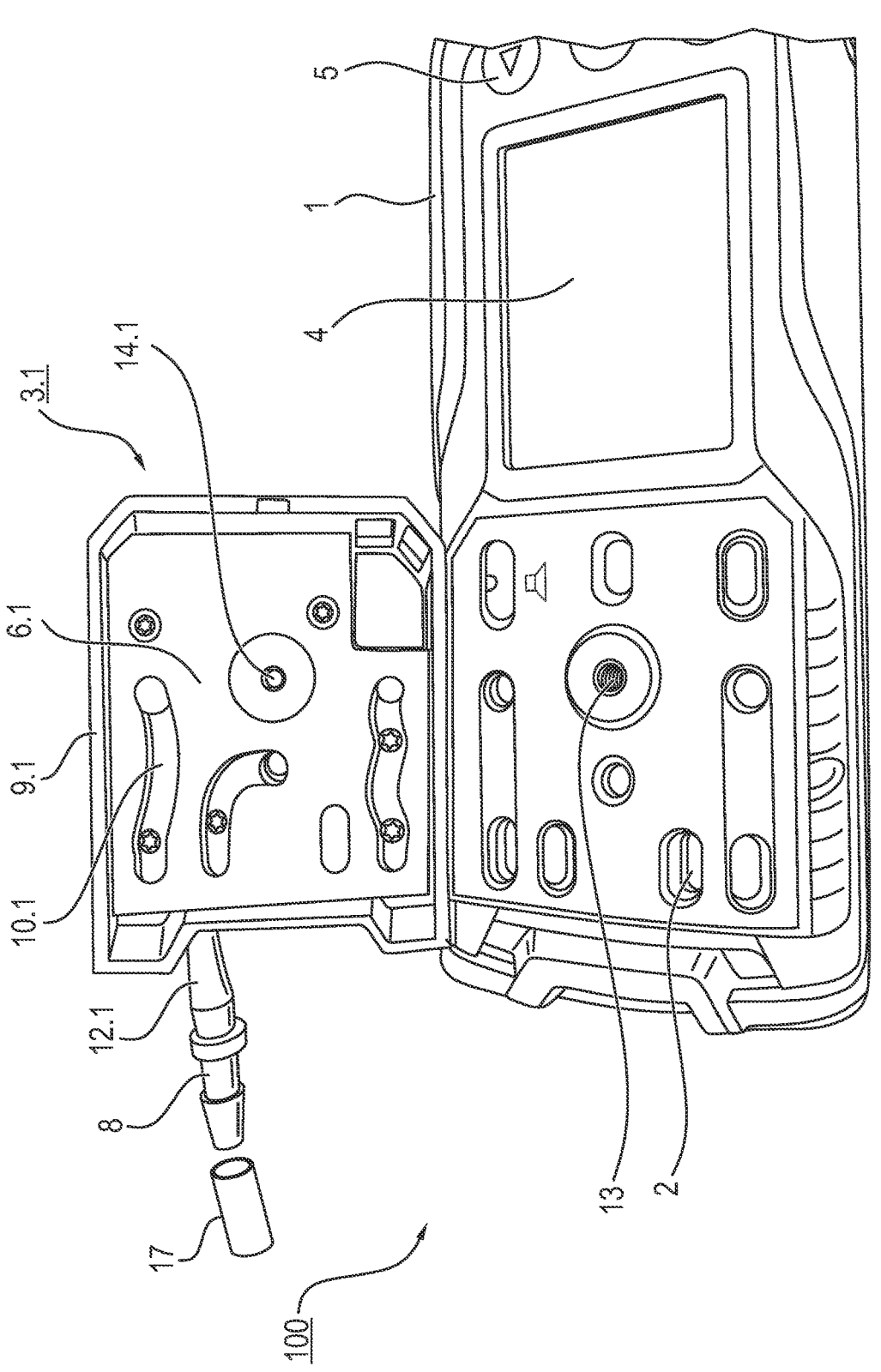
FIG. 4 is a perspective view showing the gas detector of FIG. 1 before attaching the calibration adapter.

FIG. 4 shows the calibration adapter 3.1 (top) and the rest of the gas detector 100 (bottom) before the calibration adapter 3.1 is placed on the housing 1. The filling 6.1 points towards the viewer.

Figure 5:
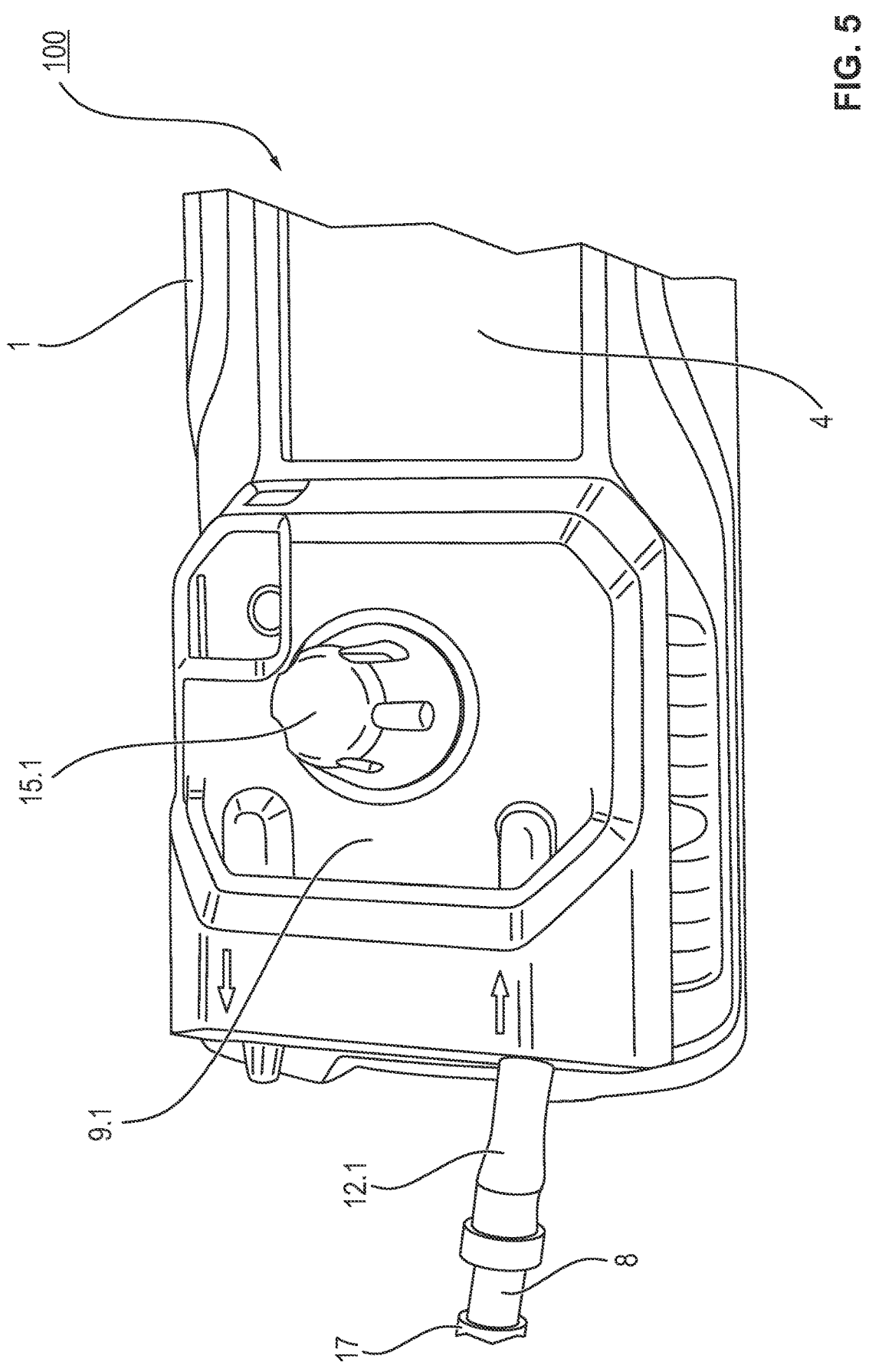
FIG. 5 is a perspective view of the gas detector of FIG. 4 after the calibration adapter has been fitted.

FIG. 5 shows the gas detector 100 with the attached calibration adapter 3.1. The calibration adapter 3.1 covers the inlets 2. The outer shell 9.1 faces the viewer. A knob 15.1 is rotatably connected to the outer shell 9.1 as well as non-rotatably connected to the screw 14.1 and allows the screw 14.1 to be turned from the outside. Furthermore, the connecting piece (nozzle) 12.1 and the calibration connection element 8 can be seen.

While specific embodiments of the invention have been shown and described in detail to illustrate the application of the principles of the invention, it will be understood that the invention may be embodied otherwise without departing from such principles.

---

List of reference numbers

| | |
|---|---|
| 1 | Housing of the gas detector 100, accommodates the display unit 4 and the operating elements 5, has the inlets 2 and the thread 13 |
| 2 | Inlets in housing 1 |
| 3 | Adapter, includes the outer shell 9, the filling 6 and the nozzle 12, can be detachably attached to the housing 1, is used when the gas detector 100 is deployed |
| 3.1 | Calibration adapter, includes the outer shell 9.1, the filling 6.1 and the nozzle 12.1, can be detachably attached to housing 1, is used in a calibration of gas detector 100 |
| 4 | Display unit in the housing 1, visually displays measurement results |
| 5 | Operating elements in the housing 1 |
| 6 | Filling of the adapter 3, is made of a foam with fluorinated rubber |
| 6.1 | Filling of the calibration adapter 3.1, is made of a foam with fluorinated rubber |
| 7 | Connection element that can be placed on the nozzle 12 |
| 8 | Connection element that can be placed on the nozzle 12.1 and connected to a calibration station |
| 9 | Outer shell of the adapter 3 |
| 9.1 | Outer shell of the adapter 3.1 |
| 10 | Fluid channels in the filling 6 |
| 10.1 | Fluid channels in the filling 6.1 |
| 11 | Area above the inlets 2 covered by the attached adapter 3, 3.1 |
| 12 | Nozzle on outer shell 9 |
| 12.1 | Nozzle on the outer shell 9.1 |
| 13 | Thread in housing 1 into which the screw 14, 14.1 can be screwed in |
| 14 | Screw of adapter 3, can be screwed into thread 13 |
| 14.1 | Screw of the calibration adapter 3.1, can be screwed into the thread 13 |
| 15.1 | Knob for the screw 14.1 |
| 16 | Hose that can be placed on the connection element 7 |
| 17 | Hose that can be placed on the connection element 8 |
| 100 | Gas detector, includes housing 1, adapter 3, 3.1, display unit 4 and operating elements 5, thread 13 and sensors not shown |

What is claimed is:

1. A gas detector comprising: a housing with an inlet; a sensor inside the housing, wherein the inlet is adapted to provide a fluid connection between an environment of the gas detector and the sensor inside the housing, wherein the sensor is configured to measure a detection variable that correlates with a presence and/or a concentration of at least one target gas to be detected; and an adapter configured to be fluid-tightly detachably mountable on the housing or mountable on the housing and removable or detachable again, wherein the adapter in a mounted state fluid-tightly separates the inlet from the environment and in a state with the adapter removed, the inlet establishes the fluid connection between the environment and the sensor, the adapter comprising: a connection element for connecting a fluid guide unit; an outer shell; and an elastic filling, wherein, with the adapter in the mounted state, the filling is located between the outer shell and the sensor inside the housing, wherein the filling is made of a cured foam, wherein the foam comprises at least one fluorinated rubber, wherein a channel configuration is defined and recessed in the filling, and wherein the channel configuration establishes a fluid connection between the connection element and the sensor.

2. A gas detector according to claim 1, wherein:
the adapter is a first adapter;
the gas detector further comprises a second adapter that is configured to be fluid-tightly detachably mountable or mountable on the housing and removable or detachable again; and
one of the first adapter and the second adapter is selectively fluid-tightly mounted on the housing.

3. A gas detector according to claim 2, further comprising a fluid guide unit wherein:
the first adapter is connected or configured to be connected to a fluid guide unit to establish a fluid connection; and
the second adapter is connected or configured to be connected to a gas detector calibration device.

4. A gas detector according to claim 1, wherein the filling provides a wall for the channel configuration.

5. A gas detector according to claim 1, wherein:
the outer shell is curved and encloses a space; and
the filling completely fills the space enclosed by the outer shell except for the channel configuration.

6. A gas detector according to claim 1, further comprising a second sensor in the housing, wherein:
the housing has a second inlet;
the second inlet is adapted to provide a fluid connection between an environment of the gas detector and the second sensor inside the housing;
the second sensor is configured to measure a detection variable that correlates with a presence and/or a concentration of at least one target gas to be detected; and
the channel configuration establishes a fluid connection between the connection element and the other sensor.

7. A gas detector according to claim 1, wherein the cured foam defines the channel configuration, the channel configuration defining a fluid flow path for transporting fluid from the connection element to the sensor, wherein the fluid flow path extends through the cured foam.

8. A gas detector kit comprising: a gas detector comprising a housing with an inlet; and a sensor inside the housing, wherein the inlet is adapted to provide a fluid connection between an environment of the gas detector and the sensor inside the housing, wherein the sensor is configured to measure a detection variable that correlates with a presence and/or a concentration of at least one target gas to be detected; and an adapter configured to be fluid-tightly detachably mountable on the housing or mountable on the housing and removable or detachable again, wherein the adapter in amounted state fluid-tightly separates the inlet from the environment and in a state with the adapter removed, the inlet establishes the fluid connection between the environment and the sensor, the adapter comprising: a connection element for connecting a fluid guide unit; an outer shell; and an elastic filling, wherein, with the adapter in the mounted state, the filling is located between the outer shell and the sensor inside the housing, wherein the filling is made of a cured foam, wherein the foam comprises at least one fluorinated rubber, wherein a channel configuration is defined and recessed in the filling, and wherein the channel configuration establishes a fluid connection between the connection element and the sensor.

9. A gas detector kit according to claim 8, further comprising a second adapter that is configured to be fluid-tightly detachably mountable or mountable on the housing and removable or detachable again, wherein one of the adapter and the second adapter is selectively fluid-tightly mounted on the housing.

10. A gas detector kit according to claim 9, further comprising a fluid guide unit wherein:
the adapter is configured to be connected to a fluid guide unit to establish a fluid connection; and
the second adapter is configured to be connected to a gas detector calibration device.

11. A gas detector kit according to claim 8, wherein the filling provides a wall for the channel configuration.

12. A gas detector kit according to claim 8, wherein:
the outer shell is curved and encloses a space; and
the filling completely fills the space enclosed by the outer shell except for the channel configuration.

13. A gas detector kit according to claim 8, wherein:
the gas detector comprises a second sensor in the housing, wherein:
the housing has a second inlet;
the second inlet is adapted to provide a fluid connection between an environment of the gas detector and the second sensor inside the housing;
the second sensor is configured to measure a detection variable that correlates with a presence and/or a concentration of at least one target gas to be detected; and
the channel configuration establishes a fluid connection between the connection element and the second sensor.

14. A gas detector process comprising the steps of: providing a gas detector comprising a housing with an inlet; and a sensor inside the housing, wherein the inlet is adapted to provide a fluid connection between an environment of the gas detector and the sensor inside the housing, wherein the sensor is configured to measure a detection variable that correlates with a presence and/or a concentration of at least one target gas to be detected; and providing an adapter configured to be fluid-tightly detachably mountable on the housing or mountable on the housing and removable or detachable again, wherein the adapter in a mounted state fluid-tightly separates the inlet from the environment and in a state with the adapter removed, the inlet establishes the fluid connection from the environment to the sensor, the adapter comprising: a connection element for connecting a fluid guide unit; an outer shell; and an elastic filling, wherein, with the adapter in the mounted state, the filling is located between the outer shell and the sensor inside the housing, wherein the filling is made of a cured foam, wherein the foam comprises at least one fluorinated rubber, wherein a channel configuration is defined and recessed in the filling, and wherein the channel configuration establishes a fluid connection between the connection element and the sensor; and selectively operating the sensor with the adapter in either the mounted state or in the state with the adapter removed.

15. A gas detector process according to claim 14, further comprising:

providing a second adapter that is configured to be fluid-tightly detachably mountable or mountable on the housing and removable or detachable again, wherein one of the adapter and the second adapter is selectively fluid-tightly mounted on the housing; and selectively operating the sensor with the second adapter in either the mounted state or in the state with the second adapter removed.

16. A gas detector process according to claim 15, further comprising providing a fluid guide unit wherein: the adapter is configured to be connected to a fluid guide unit to establish a fluid connection; and the second adapter is configured to be connected to a gas detector calibration device.

17. A gas detector process according to claim 15, wherein the filling provides a wall for the channel configuration.

18. A gas detector process according to claim 15, wherein:

the outer shell is curved and encloses a space; and the filling completely fills the space enclosed by the outer shell except for the channel configuration.

19. A gas detector process according to claim 15, wherein:

the gas detector comprises a second sensor in the housing, wherein:

the housing has a second inlet;

the second inlet is adapted to provide a fluid connection between an environment of the gas detector and the second sensor inside the housing;

the second sensor is configured to measure a detection variable that correlates with a presence and/or a concentration of at least one target gas to be detected; and the channel configuration establishes a fluid connection between the connection element and the second sensor.

20. A gas detector process according to claim 14, wherein the cured foam defines the channel configuration, the channel configuration defining a fluid flow path for transporting fluid from the connection element to the sensor, wherein the fluid flow path extends through the cured foam.

* * * * *